(12) United States Patent
Kato et al.

(10) Patent No.: US 8,486,916 B2
(45) Date of Patent: Jul. 16, 2013

(54) MEDICINE, FOOD AND DRINK OR FEED CONTAINING SPHINGOMYELIN

(71) Applicant: Megmilk Snow Brand Co., Ltd., Sapporo (JP)

(72) Inventors: Ken Kato, Kawagoe (JP); Susumu Miura, Kawagoe (JP); Leo Tanaka, Kawagoe (JP); Hiroshi Ueno, Kawagoe (JP); Noriko Ueda, Kawagoe (JP); Yuko Haruta, Kawagoe (JP); Toshimitsu Yoshioka, Kawagoe (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 0 days.

(21) Appl. No.: 13/676,430

(22) Filed: Nov. 14, 2012

(65) Prior Publication Data

US 2013/0079307 A1    Mar. 28, 2013

Related U.S. Application Data

(63) Continuation of application No. 11/992,365, filed as application No. PCT/JP2006/318888 on Sep. 22, 2006, now abandoned.

(30) Foreign Application Priority Data

Sep. 22, 2005  (JP) .................. 2005-276632
Mar. 14, 2006  (JP) .................. 2006-068501
Sep. 21, 2006  (JP) .................. 2006-256536

(51) Int. Cl.
*A61K 31/685* (2006.01)
*A23J 7/00* (2006.01)

(52) U.S. Cl.
USPC ............. 514/77; 514/811; 514/75; 514/76; 514/78; 514/613; 514/556; 554/80; 554/41

(58) Field of Classification Search
None
See application file for complete search history.

(56) References Cited

U.S. PATENT DOCUMENTS 7,288,534 B2    10/2007    Modrak et al.

FOREIGN PATENT DOCUMENTS

| EP | 0730032 A2 | 9/1996 |
|---|---|---|
| EP | 1618876 A1 | 1/2006 |
| GB | 1259197 A | 1/1972 |
| JP | 6416708 A | 1/1989 |
| JP | 6416709 A | 1/1989 |

(Continued)

OTHER PUBLICATIONS

Pittler, M.H. et al., Interventions for Preventing or Treating Alcohol Hangover: systematic review of randomized controlled trials, 2005, BMJ, vol. 331, pp. 1-4.

(Continued)

*Primary Examiner* — Yate K Cutliff
(74) *Attorney, Agent, or Firm* — Sughrue Mion, PLLC

(57) ABSTRACT

It is intended to find novel pharmaceutical use of sphingomyelin and to provide preventive or therapeutic agents for various diseases as well as a food and drink product and feed comprising any of these agents. The present invention provides a pharmaceutical agent which contains sphingomyelin as an active ingredient and is any of the following agents: 1) a sialomucin secretion promoter, 2) an agent for preventing drunken sickness (hangover), 3) an antiallergic agent, 4) an antioxidant, 5) an agent for defending against infection, 6) a hair growth agent, 7) a therapeutic agent for demyelinating disease, 8) an anti-pigmentation agent, 9) an anti-inflammatory agent, and 10) an agent for improving learning ability. The present invention also provides a food and drink product or feed, characterized by comprising the agent. It is preferred that the sphingomyelin should be derived from milk.

4 Claims, 1 Drawing Sheet

FOREIGN PATENT DOCUMENTS

| | | | |
|---|---|---|---|
| JP | 6211668 A | 8/1994 |
| JP | 7133217 A | 5/1995 |
| JP | 8259988 A | 10/1996 |
| JP | 10175868 A | 6/1998 |
| JP | 10194957 A | 7/1998 |
| JP | 2001128642 A | 5/2001 |
| JP | 2001158735 A | 6/2001 |
| JP | 2001158736 A | 6/2001 |
| JP | 2001278750 A | 10/2001 |
| JP | 2003146883 A | 5/2003 |
| JP | 2003252765 A | 9/2003 |
| JP | 2004231544 A | 8/2004 |
| JP | 2005187341 A | 7/2005 |
| WO | 2004064820 A2 | 8/2004 |
| WO | 2004064847 A1 | 8/2004 |
| WO | 2007034927 A1 | 3/2007 |

OTHER PUBLICATIONS

Swift, R. et al., Alcohol Hangover, 1998, Alcohol & Health Research World, vol. 22, No. 1, pp. 54-60.

Xerri, L. et al., "Predominance of Siamolucin Secretion in Malignant and Premalignant Pancreatic Lesions" Human Pathology, Sep. 1, 1990, pp. 927-931, vol. 21, No. 9, Saunders, Philadelphia, PA.

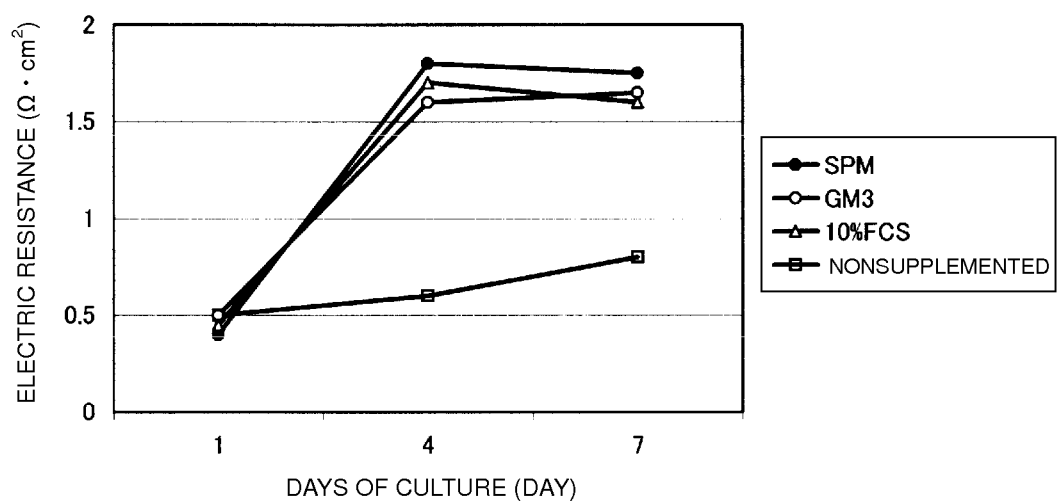

MEDICINE, FOOD AND DRINK OR FEED CONTAINING SPHINGOMYELIN

CROSS REFERENCE TO RELATED PATENT APPLICATIONS

The present application is a Continuation application of U.S. patent application Ser. No. 11/992,365, filed Oct. 12, 2009, which is a 371 of PCT/JP2006/318888 filed Sep. 22, 2006, which claims priority of Japanese Patent Application Nos. 2005-276632 filed Sep. 22, 2005, 2006-068501 filed Mar. 14, 2006, and 2006-256536 filed Sep. 21, 2006; the above noted applications are incorporated herein by reference in their entirety.

TECHNICAL FIELD

The present invention relates to a pharmaceutical agent which contains sphingomyelin and has novel use. More specifically, the present invention relates to a pharmaceutical agent which contains sphingomyelin and is a sialomucin secretion promoter, an agent for preventing drunken sickness (hangover), an antiallergic agent, an antioxidant, an agent for defending against infection, a hair growth agent, a therapeutic agent for demyelinating disease, an anti-pigmentation agent, an anti-inflammatory agent, or an agent for improving learning ability, and to a food and drink product or feed comprising any of these agents.

BACKGROUND ART

Sphingomyelin is a type of phospholipid found abundantly in milk and accounts for approximately 30% of phospholipids in cow milk. Sphingomyelin has a structure in which phosphocholine is bound with a ceramide skeleton composed of sphingosine and fatty acid, and has been known to be also found in the brain or nervous tissues. Moreover, sphingomyelin has been reported to be also contained in small amounts in food such as yolk.

Sphingomyelin has been known to influence cell growth or differentiation in vivo via the signal transduction system. Moreover, it has also been suggested that sphingomyelin has an effect of suppressing reduction in protein kinase C activity attributed to aging and is effective for the prevention or treatment of Alzheimer-type memory disorder (Patent Document 1). However, its effect of improving learning ability in a general sense has not been known by any means. It has further been known that sphingomyelin has an effect of improving lipid digestion/absorption function associated with aging (Patent Document 2). However, its other effects have been little known. Therefore, the development of a pharmaceutical agent, a food and drink product, or feed comprising sphingomyelin as an active ingredient has been expected.
Patent Document 1: Japanese Patent Laid-Open No. 2003-146883
Patent Document 2: Japanese Patent Laid-Open No. 11-269074

DISCLOSURE OF THE INVENTION

Problem to be Solved by the Invention

An object of the present invention is to find novel pharmaceutical use of sphingomyelin and to provide a pharmaceutical agent which is effective as preventive or therapeutic agents for various diseases as well as a food and drink product and feed comprising any of these agents.

Means of Solving the Problem

To attain the object, the present inventors have examined the pharmacological effects of sphingomyelin in various ways and have consequently completed the present invention by finding that sphingomyelin has an effect of promoting sialomucin secretion, an effect of preventing drunken sickness (hangover), an antiallergic effect, an antioxidative effect, an effect of defending against infection, a hair growth effect, a therapeutic effect on demyelinating disease, an anti-pigmentation effect, an anti-inflammatory effect, or an effect of improving learning ability as novel use.

Specifically, the present invention provides a pharmaceutical agent which contains sphingomyelin as an active ingredient and is any of the following agents: 1) a sialomucin secretion promoter, 2) an agent for preventing drunken sickness (hangover), 3) an antiallergic agent, 4) an antioxidant, 5) an agent for defending against infection, 6) a hair growth agent, 7) a therapeutic agent for demyelinating disease, 8) an anti-pigmentation agent, 9) an anti-inflammatory agent, and 10) an agent for improving learning ability.

The present invention also provides the pharmaceutical agent, characterized in that the sphingomyelin is derived from milk.

The present invention also provides a food and drink product or feed, characterized by comprising the agent.

Effects of the Invention

According to the present invention, sphingomyelin can be used as 1) a sialomucin secretion promoter, 2) an agent for preventing drunken sickness (hangover), 3) an antiallergic agent, 4) an antioxidant, 5) an agent for defending against infection, 6) a hair growth agent, 7) a therapeutic agent for demyelinating disease, 8) an anti-pigmentation agent, 9) an anti-inflammatory agent, or 10) an agent for improving learning ability.

BRIEF DESCRIPTION OF THE DRAWINGS

FIG. 1 is a graph showing results of testing tight junction formation according to the present invention.

BEST MODE FOR CARRYING OUT THE INVENTION

Sphingomyelin that can be used in the present invention is not particularly limited and is chemically synthesized or naturally occurring sphingomyelin including those derived from milk such as cow milk or goat milk and those derived from yolk such as hen's egg yolk. Sphingomyelin derived from milk is more preferable. Among those derived from milk, a sphingomyelin raw material derived from cow milk has a sphingomyelin content corresponding to a concentration as high as 25% or more and is available inexpensively on the market. Therefore, such a sphingomyelin raw material is particularly preferable.

In this context, the sphingomyelin may be used in a more highly pure form obtained by purification or may be used in a form of sphingomyelin-containing phospholipid.

For the sphingomyelin or the sphingomyelin-containing phospholipid, for example, sphingomyelin-containing phospholipid derived from milk (sphingomyelin content of approximately 28% by weight in phospholipid) can be used which is obtained by a method comprising subjecting milk or a dairy product such as a whey protein concentrate (WPC) to ether or acetone extraction (Japanese Patent Laid-Open No. 3-47192). Alternatively, a butter curd or serum-containing aqueous fraction obtained by heat-melting butter can be used as sphingomyelin-containing phospholipid (sphingomyelin content of approximately 9% by weight in phospholipid). Furthermore, a milk fat globule membrane fraction contained in butter milk or serum can be used as sphingomyelin-containing phospholipid (sphingomyelin content of approximately 9% by weight in phospholipid). More highly pure sphingomyelin may be used which is obtained by purifying these sphingomyelin-containing phospholipids by an approach such as dialysis, ammonium sulfate fractionation, gel filtration, isoelectric precipitation, ion-exchange chromatography, or solvent fractionation.

A pharmaceutical agent of the present invention can be used as a preparation having any of various dosage forms. Such dosage forms are not particularly limited. Thus, the sphingomyelin and/or the sphingomyelin-containing phospholipid can be formulated into preparations in various dosage forms such as tablets, capsules, granules, powder materials, powdered medicines, and liquid medicines (e.g., syrups).

Likewise, the type of a food and drink product of the present invention is not particularly limited. The agent of the present invention can be formulated into food or drink products (e.g., cow milk, processed milk, milk drinks, yogurt, soft drinks, coffee drinks, juice, cheese, jelly, wafers, biscuits, bread, noodles, and sausages) or nutritional foods, and further into nutritional supplementary compositions. Moreover, the type of feed of the present invention is not particularly limited.

In this context, the pharmaceutical agent, the food and drink product, and the feed of the present invention can be produced by a standard method except that it contains sphingomyelin.

In the present invention, to exhibit each pharmacological effect, for example, the amount of sphingomyelin formulated into the pharmaceutical agent, the food and drink product, or the feed may be adjusted so that approximately 0.1 to 100 mg of sphingomyelin per day can be ingested generally, though the amount differs depending on use.

EXAMPLES

Hereinafter, the present invention will be described more specifically with reference to Examples and Test Examples. The term "%" in Examples and Test Examples means "% by weight", unless otherwise specified.

Example 1

A reaction solution obtained by allowing protease to act on a 10% aqueous solution of a whey protein concentrate (WPC) was subjected to extraction with a chloroform-methanol (2:1) solution, and the extract was then concentrated and further subjected to acetone extraction to obtain a complex lipid fraction. Next, this complex lipid fraction was subjected to stepwise extraction with a chloroform-methanol solution using Florisil column chromatography to obtain a phospholipid fraction. This phospholipid fraction was subjected to stepwise extraction with a chloroform-methanol solution using silica gel chromatography to obtain a fraction, which was then freeze-dried to obtain a sphingomyelin raw material. This sphingomyelin raw material was treated by thin-layer chromatography, followed by color development with a Dittmer reagent. A sphingomyelin content measured by a densitometry method was 95.2%. This sphingomyelin raw material can be used directly as an agent of the present invention.

Test Example 1

Sphingomyelin was tested for its effect of promoting sialomucin secretion using the method described in "Test Example 1" of Japanese Patent Laid-Open No. 2001-206848.

Specifically, an AIN-93G standard diet was administered as feed to a control group (Control); this standard diet whose sucrose was partially substituted with 1% of the sphingomyelin raw material described in Example 1 in the present specification was administered as feed to a sphingomyelin administration group (SPM); and this standard diet whose sucrose was partially substituted with 1% of sialyllactose was administered as feed to a sialyllactose administration group (SL).

Seven-week-old male SD rats (manufactured by Charles River Laboratories, Japan, Inc) were raised under conditions involving humidity of 60%, room temperature of 24° C., and light-dark (12 hour/12 hour) control. All the rats were preliminarily raised for 1 week with a standard diet and then divided into 3 groups each containing 12 individuals. These groups were allowed to freely take their respective experimental diets and raised for 1 week. Rat saliva was collected on the 7th day after the administration of experimental diets. A sialomucin content in the saliva was measured by high-performance liquid chromatography. The results of measuring a sialomucin content in the saliva of each experimental group is shown in Table 1. As is evident from the results shown in Table 1, the sialomucin content in the sphingomyelin administration group was significantly larger than that in the control group and was also larger than that in the sialyllactose administration group.

TABLE 1

| Administration group | Sialomucin content (μg/μl) |
|---|---|
| Control | 21.3 ± 3.5 |
| SPM | 25.2 ± 2.9 |
| SL | 24.9 ± 3.1 |

Test Example 2

Sphingomyelin was tested for its effect of promoting sialomucin secretion using the method for testing inhibitory activity against cholera toxin binding described in "Test Example 2" of Japanese Patent Laid-Open No. 2001-206848.

The saliva of each experimental group of Test Example 1 in the present specification was used to examine inhibitory activity against cholera toxin binding. 200 μl of an ethanol solution containing 0.1% ganglioside GM1 (w/v) was added to a 96-well plate for ELISA test. Then, the ganglioside GM1 was adsorbed thereonto by air-drying. The saliva of each experimental group was diluted 10 times with PBS containing 1% bovine serum albumin (BSA) and then reacted for 1 hour by the addition of a biotin-conjugated cholera toxin. 100 μl of the reaction solution was added to the plate for ELISA test, and the plate was left for 30 minutes. Then, the supernatant was removed. The plate for ELISA test was washed several times with PBS containing 0.05% Tween 20. Biotin-binding β-galactosidase was added thereto. The plate for ELISA test was left for a given length of time. Then, the supernatant was removed. The plate for ELISA test was washed several times again with PBS containing 0.05% Tween 20, and the contents in the plate were reacted for 30 minutes by the addition of 4-methylumbelliferyl galactose. Then, 4-methylumbelliferone produced was measured with a fluorophotometer (excitation wavelength: 360 nm, measurement wavelength: 460 nm). Then, an inhibition rate was calculated according to the following formula:

Inhibition rate(%)={1−(A/B)}×100, wherein

A represents the fluorescence intensity of the sphingomyelin administration group (SPM) or sialyllactose administration group (SL), and B represents the fluorescence intensity of the control group (Control).

The results are shown in Table 2. As is evident from the results of Table 2, it was demonstrated that the inhibitory activity of the sphingomyelin administration group against cholera toxin binding is much higher than that of the control group. It was further demonstrated that the inhibitory activity of the sphingomyelin administration group against cholera toxin binding is also higher than that of the sialyllactose administration group. Thus, it was demonstrated that orally taken sphingomyelin increases a sialomucin content in saliva and as a result, also enhances toxin-neutralizing ability.

TABLE 2

| Administration group | Inhibition rate (%) |
|---|---|
| Control | 31.4 ± 3.0 |
| SPM | 38.9 ± 3.8 |
| SL | 37.9 ± 2.9 |

In this context, a sialomucin content in the saliva was measured by the following method:

(1) Collection of Saliva 0.2 ml of a Nembutal solution was intramuscularly injected to rats fasted for 2 hours or longer. After anesthesia, a solution of pilocarpine hydrochloride serving as a saliva secretion promoter was intramuscularly injected thereto. After 3 minutes, saliva secreted beneath the rat tongue was collected into a microtube using an autopipette, and this procedure was performed for exactly 9 minutes. After the completion of saliva collection, the saliva collection was terminated by the injection of 0.1 ml of 0.1% atropine sulfate serving as a saliva secretion inhibitor.

(2) Collection of Sialomucin Fraction

The collected saliva was rapidly stored at a low temperature of 0° C. or lower and then treated using a centrifuge (11,000 rpm, 60 min.) cooled to 4° C. to obtain a supernatant. The supernatant was dialyzed against a saline for 3 days using a micro-dialysis tube with a molecular weight cut off of 100,000 to collect the content solution as a sialomucin fraction in the saliva.

(3) Quantification of Sialomucin Content

A sialomucin content in the sialomucin fraction was quantified with a Sialic Acid Fluorescence Labeling Kit (Takara Bio Inc.). An aliquot of the sialomucin fraction was collected into a test tube and dried under reduced pressure using a rotary evaporator. Then, the dried product was hydrolyzed at 80° C. for 3 hours by the addition of 2 N acetic acid. Free N-acetyl sialic acid or O-acetylated sialic acid was reacted at 55° C. for 2.5 hours by the addition of a DMB reagent as a fluorescence labeling agent and then quantified by high-performance liquid chromatography.

Test Example 3

Sphingomyelin was tested for its effect of preventing drunken sickness (hangover) using the method described in "Example 1" of Japanese Patent Laid-Open No. 2001-199880.

Male Wistar rats were preliminarily raised for 1 week. Then, the rats of 110 to 120 g in body weight were used. The rats were fasted overnight before the experiment and given neither food nor water during the experiment. The rats were divided into an alcohol single administration group (control group) and a sphingomyelin administration group. Each group contained 5 individuals.

10 ml/kg of an aqueous solution containing 40 (v/v) % ethyl alcohol was orally administered to the alcohol single administration group (control group), and 10 ml/kg of an aqueous solution containing 40 (v/v) % ethyl alcohol and 2 mg/kg of the sphingomyelin raw material of Example 1 in the present specification were orally administered to the sphingomyelin administration group. After administration, the rats were observed until they recovered from drunken symptoms.

As a result, the alcohol single administration group (control group) spent 5 hours to recover from drunken symptoms and was observed to exhibit lying in a prone position, staggering gait, and reduced grip strength as symptoms after administration. By contrast, the sphingomyelin administration group recovered from drunken symptoms within 1 hour and exhibited only staggering gait as symptoms after administration. This demonstrated that sphingomyelin has a significant effect of preventing drunken sickness (hangover) symptoms caused by drinking.

Test Example 4

Test on Tight Junction Formation

Sphingomyelin was tested for its antiallergic effect using the method described in "Test Example 1" of Japanese Patent Laid-Open No. 8-109133.

Ganglioside GM3 (manufactured by Sigma) or the sphingomyelin raw material of Example 1 in the present specification was added at a concentration of 2 μg/ml (medium) to a serum-free medium Cosmedium 001 (manufactured by Cosmo Bio Co., Ltd.). Millicell-CM (manufactured by Millipore; pore size: 0.4 μm; 0.6 cm$^2$) was set in a 24-well micro-titer plate. The membrane surface was treated with collagen (manufactured by Koken Co., Ltd.). Then, a human colon adenocarcinoma cell line Caco-2 was cultured. Culture in a medium supplemented with 10% FCS (10% FCS) and culture in only Cosmedium 001 (nonsupplemented) were compared in the following point: an electric resistance measurement apparatus Millicell-ERS (manufactured by Millipore) was used to measure electric resistance (R) values inside or outside Millicell-CM on the 1st, 4th, and 7th days of culture. The results are shown in FIG. 1. As is evident from the results shown in FIG. 1, the R value was increased in the sphingomyelin-supplemented medium (SPM), as in the ganglioside GM3-supplemented medium (GM3) or the 10% FCS-supplemented medium. This suggests that the tight junction of Caco-2 proceeds in the sphingomyelin-supplemented and GM3-supplemented media, resulting in reduction in intercellular spaces. By contrast, the R value was not increased in the nonsupplemented medium. Thus, it was demonstrated that sphingomyelin has an effect of forming the tight junction of intestinal mucosal cells and has an antiallergic effect brought about by the prevention of allergens from invading living bodies.

Test Example 5

Test on Promotion of Secretory IgA Production

Sphingomyelin was tested for its antiallergic effect using the method described in "Test Example 2" of Japanese Patent Laid-Open No. 8-109133.

5 ml of aseptically collected human milk was diluted twice with a 10 mM phosphate-buffered saline (PBS, pH 7.2) containing 150 mM NaCl and then layered in a test tube containing 5 ml of a separation solution (mixed solution of 33.4% Conray 400 (manufactured by Daiichi Pharmaceutical Co., Ltd.) and 9% Ficoll (manufactured by Pharmacia) at a ratio of 5:12). After centrifugation at 400×G for 30 minutes, the intermediate layer in which lymphocytes were gathered was collected with a Pasteur pipette. The lymphocytes were dispersed and washed in 10 ml of PBS and then centrifuged at 150×G for 10 minutes. This washing procedure was repeated three times. Then, 12 ml of an RPMI-1640 medium containing insulin (10 μg/ml) and transferrin (5 μg/ml) was added thereto, and the mixture was dispensed in an amount of 3 ml/Petri dish into 3 Petri dishes (A; B; and C). 0.3 ml of fetus calf serum (FCS) was added to the Petri dish A; 3 μg of the sphingomyelin raw material of Example 1 in the present specification was added to the Petri dish B; and the Petri dish C was nonsupplemented.

After 7 days, an IgA content in the culture solution was 3.89 μg/ml in the Petri dish A, 3.11 μg/ml in the Petri dish B, and less than 0.1 μg/ml in the Petri dish C. The Petri dishes A and B exhibited a high IgA yield, whereas the Petri dish C had little IgA production. This result demonstrated that sphingomyelin has an effect of enhancing the IgA producing ability of lymphocytes and has an antiallergic effect.

Test Example 6

Test on Effect of Blocking Allergen Invasion

Sphingomyelin was tested for its antiallergic effect using the method described in "Test Example 3" of Japanese Patent Laid-Open No. 8-109133.

Infant Wistar rats (14 day old, body weight: around 20 g, 8 individuals, Charles River Laboratories, Japan) were divided into a control group and sphingomyelin administration groups (SPM administration groups), and all the groups were raised using artificial milk having composition closely analogous to that of rat milk. On the 14th to 20th days, a sphingomyelin solution (1 mg/ml) prepared from the sphingomyelin raw material of Example 1 in the present specification was orally administered at a daily dose of 50 μl to the SPM administration groups using a micropipette. On the 21st day, 100 μl of a β-Lg solution (10 mg/ml) was orally administered thereto. Blood collected from the rats after 1 hour and after 2 weeks. On the other hand, a β-Lg solution and a complete Freund adjuvant were mixed for emulsification, and the emulsion was hypodermically injected to 3 locations (both sides of the back, and the hip) of a 3-month-old rabbit (Japanese white, male, manufactured by KITAYAMA LABES Co., Ltd.) to obtain anti-β-Lg serum. A β-Lg amount in the above-described blood after 1 hour was measured by a sandwich ELISA method using this antiserum as a primary antibody and a horseradish peroxidase (PO)-labeled secondary antibody. Moreover, anti-β-Lg IgE in the above-described blood after 2 weeks was measured by an ELISA method using β-Lg and a PO-labeled anti-rat IgE antibody (manufactured by Nordic). The results are shown in Table 3 below. As is evident from the results shown in Table 3, the mucosal permeability of β-Lg in the digestive tract of the groups to which sphingomyelin was administered at a dose of 0.1 mg/kg (body weight)/day or more was observed to be significantly smaller than that in the control group, showing suppressed IgE production. Therefore, it was demonstrated that sphingomyelin has an antiallergic effect.

TABLE 3

Results of measuring β-Lg and anti-β-Lg antibody in blood

| | β-Lg(ng/ml) | Anti-β-Lg IgE (ng/ml) |
|---|---|---|
| Control group | 35.7 ± 16.9 | 470.5 ± 98.7 |
| SPM administration group (0.05 mg/kg/day) | 38.6 ± 14.7 | 498.2 ± 156.8 |
| SPM administration group (0.1 mg/kg/day) | 13.4 ± 6.6 | 190.6 ± 77.8 |
| SPM administration group (5.0 mg/kg/day) | 5.6 ± 3.8 | 165.4 ± 65.9 |

Mean ± standard deviation (n = 2)

Test Example 7

Sphingomyelin was tested for its antioxidative effect according to the method described in "Test Example 1" of Japanese Patent Laid-Open No. 11-209756.

The antioxidative activity of sphingomyelin was measured according to the method of Osawa et al. (J. Agric. Food Chem., vol. 35, pp. 809-812, 1987). Specifically, preserved rabbit blood was mixed with an equal amount of an isotonic solution (10 mM phosphate buffer/152 mM sodium chloride, pH 7.4), followed by centrifugation at 1,500×g (3,500 rpm) at 4° C. for 20 minutes. Blood corpuscles washed by repeating this procedure three times were mixed with an equal amount of a hypotonic solution (10 mM phosphate buffer, pH 7.4), followed by centrifugation at 20,000×g (11,000 rpm) at 4° C. for 40 minutes. Then, loose pellets (erythrocyte membrane ghost) obtained by repeating this procedure four times were used to examine antioxidative activity. Sphingomyelin was prepared at each initial concentration of 0 mM, 0.01 mM, 0.1 mM, 1 mM, or 10 mM using the sphingomyelin raw material of Example 1 in the present specification and then mixed with the erythrocyte membrane ghost. An oxidation reaction was performed by the addition of an oxidizing agent. Subsequently, a TBA reaction was performed. Then, absorbance at 532 nm was measured to quantify an oxidation product. Then, the antioxidative activity was calculated from absorbance resulting from the addition of each sphingomyelin with respect to absorbance in the absence of added sphingomyelin defined as 100%. In this context, lower absorbance indicates more highly suppressed erythrocyte membrane ghost oxidation and higher antioxidative activity. The results are shown in Table 4. As is evident from the results shown in Table 4, it was demonstrated that sphingomyelin has a high antioxidative effect.

TABLE 4

| | Sample concentration (mM) | | | | |
|---|---|---|---|---|---|
| | 0 | 0.01 | 0.1 | 1 | 10 |
| Sphingomyelin | 100% | 98% | 95% | 80% | 61% |

Calculated with respect to absorbance in the absence of added sphingomyelin defined as 100%

Test Example 8

Sphingomyelin was tested for its antioxidative effect according to the method described in "Test Example 2" of Japanese Patent Laid-Open No. 11-209756.

The antioxidative activity of sphingomyelin was measured according to the method of Nakayama et al. (Mutation Research, vol. 281, pp. 77-80, 1992). Specifically, a Chinese hamster lung fibroblast cell line V79 was inoculated at a cell density of 200 cells/Petri dish into an MEM medium (manufactured by Flow Laboratories) containing 10% fetus calf serum and cultured at 37° C. for 5 days in the presence of 5% carbon dioxide to prepare cultured cells for test. Then, the antioxidative activity of sphingomyelin was determined using reduction in colony forming activity attributed to hydrogen peroxide as an index for toxicity and assessed based on the extent to which the colony forming activity recovered from such reduction by adding sphingomyelin to the cultured cells for test.

The cultured cells for test were inoculated onto a plate and precultured (cell adhesion) for 2 hours. Then, a sphingomyelin solution prepared at each initial concentration of 0 mM, 0.01 mM, 0.1 mM, 1 mM, or 10 mM using the sphingomyelin raw material of Example 1 in the present specification was added thereto. The cultured cells for test were incubated for 4 hours so that the cells were allowed to take up sphingomyelin, prior to hydrogen peroxide. Next, the cells were reacted for 30 minutes by the addition of hydrogen peroxide and damaged. After reaction, the cells were cultured for 5 days in a medium containing serum. In this context, the concentration of hydrogen peroxide was set to 60 μM at which colony forming activity was decreased to a few % to approximately 40%. Moreover, sphingomyelin was examined in advance for its own toxicity, and it was confirmed in advance that its own toxicity caused no reduction in colony forming activity. The antioxidative activity was evaluated by confirming colony formation after the 5-day culture and measuring the total colony count after Giemsa staining and indicated in each cell viability (%) with respect to cell viability of a sphingomyelin- and hydrogen peroxide-nonsupplemented control defined as 100%. In this context, higher cell viability indicates the higher antioxidative activity of the added sphingomyelin. The results are shown in Table 5. As is evident from the results shown in Table 5, it was demonstrated that sphingomyelin has a high antioxidative effect.

TABLE 5

| | Sphingomyelin concentration (mM) | | | | |
|---|---|---|---|---|---|
| | 0 | 0.01 | 0.1 | 1 | 10 |
| Sphingomyelin | 37% | 38% | 51% | 68% | 72% |

(Table 9)

Sphingomyelin was tested for its effect of defending against infection using the method described in Japanese Patent Laid-Open No. 62-208261.

Test on curb on incidence of diarrhea caused by enteropathogenic E. coli 30-day-old male SD rats were used as test animals. Test groups each containing 10 individuals of these rats were given feed prepared using the sphingomyelin raw material of Example 1 in the present specification so that sphingomyelin was taken at a dose of 0 (control), 0.1, 1.0, 5.0, or 10.0 mg/day. Each rat was given a fixed amount of enteropathogenic E. coli. The incidence of diarrhea was examined. The results are shown in Table 6. As is evident from Table 6, it was demonstrated that rats to which sphingomyelin has been administered at a dose of 1.0 mg/day or more have the significantly reduced incidence of diarrhea.

TABLE 6

| Test group | Intake (mg/day) | Incidence of diarrhea (%) |
|---|---|---|
| Control | | 100 |
| Sphingomyelin | 0.1 | 100 |
| | 1.0 | 40 |
| | 5.0 | 30 |
| | 10.0 | 10 |

Test Example 10

Sphingomyelin was tested for its effect of preventing enteropathogenic E. coli O-157 infection according to the method described in "Test Example 1" of Japanese Patent Laid-Open No. 2001-2704.

Test I on prevention of enteropathogenic E. coli O-157 infection 20 five-week-old BALB/c germ-free mice were allowed to orally take a saline (control group) or the sphingomyelin raw material of Example 1 in the present specification (SPM group) on a daily basis. The intake of sphingomyelin was 5 mg/day. On the 3rd day from the start of taking, the mice were infected with enteropathogenic E. coli O-157 by oral administration at a dose of $8.5 \times 10^6$ cfu/mouse. After infection, the mice were also allowed to orally take sphingomyelin on a daily basis. The mice were observed for their lives and deaths for 8 days after the administration of E. coli. The survival rate of the rats depending on the number of days after the administration of enteropathogenic E. coli O-157 is shown in Table 7. As is evident from the results of Table 7, the survival rate of the germ-free mice was enhanced by the administration of sphingomyelin.

TABLE 7

| | Survival rate (%) | | | | |
|---|---|---|---|---|---|
| | The number of days after administration of E. coli | | | | |
| | 0 | 2 | 4 | 6 | 8 |
| Control group | 100 | 65 | 50 | 40 | 35 |
| SPM group | 100 | 100 | 100 | 80 | 70 |

Test Example 11

Sphingomyelin was tested for its effect of preventing enteropathogenic E. coli O-157 infection according to the method described in "Test Example 2" of Japanese Patent Laid-Open No. 2001-2704.

Test II on prevention of enteropathogenic E. coli O-157 infection

The survival rate of mice on the 8th day after the administration of E. coli was measured in the same way as in Test Example 10 except that the intake of sphingomyelin was changed to 0.1 to 10 mg/day. The results are shown in Table 8. As is evident from the results shown in Table 8, the survival rate was significantly improved in the groups that took sphingomyelin at a dose of 1.0 mg/day or more.

TABLE 8

| Test group | Intake (mg/day) | Survival rate (%) |
|---|---|---|
| Control | | 35 |
| Sphingomyelin | 0.1 | 35 |
| | 1.0 | 65 |
| | 5.0 | 70 |
| | 10.0 | 70 |

Test Example 12

Four-week-old hairless mice (CD-1 (ICR)-nu/nu) were preliminarily raised for 1 week and then raised for 3 weeks using feed shown in Table 9. As a result, hair grew in 7 out of 10 mice in a group to which a cow milk-derived phospholipid fraction containing 15% sphingomyelin was administered at a dose of 40 mg/day (SPM group). By contrast, hair grew in only 1 out of 10 mice in a control group to which the cow milk-derived phospholipid fraction containing 15% sphingomyelin was not administered.

TABLE 9

| Ingredient | Control group | SPM group |
|---|---|---|
| Casein | 20.0 | 20.0 |
| Cow milk-derived phospholipid fraction | | 1.74 |
| Corn oil | 5.0 | 5.0 |
| DL-methionine | 0.30 | 0.30 |
| Mineral mixture | 3.50 | 3.50 |
| Vitamin mixture | 1.00 | 1.00 |
| Cellulose | 5.00 | 5.00 |
| Corn starch | 15.00 | 15.00 |
| Sucrose | 50.20 | 48.46 |
| Total | 100.00 | 100.00 |

Test Example 13

Effect of Sphingomyelin on EAE Rats

Sphingomyelin was tested for its therapeutic effect on demyelinating disease according to the method described in "Example 3" of Japanese Patent Laid-Open No. 2-250834.

A therapeutic effect on EAE rats serving as models of multiple sclerosis, one of demyelinating diseases, will be shown.

The hind footpad of Lewis rats (female, 6 week old) in groups each containing 5 individuals was immunized with a mixture of syngeneic rat brain homogenates with an equal amount of a complete Freund adjuvant (manufactured by Difco) as an antigen for inducing EAE at a dose of 80 mg in terms of the amount of the brain homogenates.

Sphingomyelin was intraperitoneally administered at a dose shown in Table 9 for 18 days from the immunization day. The measurement of body weights and the observation of EAE symptoms were performed every day. The EAE symptoms were rated by six-grade evaluation: 0: no abnormality, 1: tail paralysis, 2 tail paralysis plus hindlimb weakness, 3: tail paralysis plus hindlimb paralysis, 4: hindlimb paralysis plus forelimb weakness, and 5: hindlimb and forelimb paralysis or moribund. The therapeutic effect was assessed based on the cumulative score of the symptoms in each group.

The administration of sphingomyelin was performed by suspending the sphingomyelin raw material of Example 1 in the present specification at a concentration of 1 mg/ml or 2 mg/ml in a sterilized aqueous solution containing 0.5% methyl cellulose sodium and intraperitoneally administering this suspension to the rats. Only a saline was administered to the control group. The results are shown in Table 10 below. As is evident from the results of Table 10, sphingomyelin significantly curbed the onset of EAE as compared with the control group to which only a saline was administered. This result demonstrated that sphingomyelin can be utilized usefully in the treatment or prevention of multiple sclerosis.

TABLE 10

| | Dose (mg/kg) | Frequency of onset | The average number of days required for onset | Cumulative score of symptoms | (%) |
|---|---|---|---|---|---|
| Saline | — | 5/5 | 13.0 | 57 | 100 |
| Sphingomyelin | 1 | 2/5 | 15.2 | 10 | 18 |
| Sphingomyelin | 2 | 2/5 | 14.5 | 11 | 19 |

% represents a value with respect to the cumulative score of symptoms in the saline-administered control group defined as 100%.

Test Example 14

Inhibitory Effect of Sphingomyelin on Antibody Production

Sphingomyelin was tested for its therapeutic effect on demyelinating disease according to the method described in "Example 4" of Japanese Patent Laid-Open No. 2-250834.

A mechanism under which sphingomyelin inhibits the onset of EAE was studied. Specifically, to the rats shown in Test Example 13 to which a saline or 2 mg/kg of sphingomyelin was administered, 0.2 ml of 50% sheep red blood cell (SRBC) was intraperitoneally administered on the 14th day. The spleen was excised from each rat on the 18th day, and a single cell suspension was aseptically prepared therefrom. The red blood cells were removed by a hemolysis method. After washing with an RPMI-1640 medium, a cell suspension was prepared at a cell density of $2 \times 10^9$ cells/ml.

The number of plaque-forming cells against the sheep red blood cells was counted according to the method of Jerne and used as the number of IgM PFC. The results are shown in Table 11. From the results shown in Table 11, it was confirmed that sphingomyelin has inhibitory activity against antibody production. This suggests that sphingomyelin inhibits the onset of EAE based on this activity.

TABLE 11

| | Dose (mg/kg) | Average IgM/$10^3$ spl | (%) |
|---|---|---|---|
| Saline | — | 138 | 100 |
| Sphingomyelin | 2 | 27 | 20 |

% represents a value with respect to average IgM/$10^3$ spl in the saline-administered control group defined as 100%.

Test Example 15

Sphingomyelin was tested for its anti-pigmentation effect according to the method described in Japanese Patent Laid-Open No. 1-163112.

Using Weiser-Maples GP with phototoxic pigmentation caused by treatment with 8MOP serving as a pigmentation promoter, 50 µl of a sample was applied to an approximately 4-cm² region in the shaved back of female ICR mice (6 week old, 5 individuals per group), once daily for 8 weeks. An anti-pigmentation effect and the degree of pigmentation (shown in Table 12) produced as a side effect were rated by four-grade evaluation (+: depigmentation effect, −: side effect). The sphingomyelin raw material of Example 1 in the present specification was dissolved at a concentration of 5% and used as the sample. Moreover, no agent was applied to a control group. The results are shown in Table 13. As is evident from the results of Table 13, it was demonstrated that sphingomyelin produces no side effect and is excellent in an anti-pigmentation effect.

TABLE 12

| Assessment | Grade | Visual assessment |
|---|---|---|
| Rating of depigmentation effect | | |
| + | 3 | Whitened |
| ± | 2 | Somewhat whitened |
| −~± | 1 | Slightly whitened |
| − | 0 | Not changed |
| Side effect, pigmentation, etc. | | |
| − | 0 | Not changed |
| −~± | −1 | Somewhat blackened |
| ± | −2 | Blackened |
| + | −3 | Evidently blackened |

TABLE 13

| | Application period (week) | | | | | | | |
|---|---|---|---|---|---|---|---|---|
| | 1 | 2 | 3 | 4 | 5 | 6 | 7 | 8 |
| Sphingomyelin | 0.4 | 0.8 | 1.2 | 1.1 | 0.9 | 0.3 | 0 | 0 |
| Control | 0 | 0.2 | 0 | 0 | 0.2 | 0 | 0 | 0 |

Test Example 16

Sphingomyelin was tested for its anti-pigmentation effect by oral administration.

The back of female A-1 guinea pigs (body weight: approximately 400 g) was shaved and irradiated with ultraviolet rays (UVA (max. 360 nm): 30.3 kJ/m$^2$, UVB (max. 312 nm): 4.8 kJ/m$^2$) once daily for 4 days. Then, the guinea pigs were divided into 4 test groups (each containing 10 individuals), a group to which a saline was administered at a dose of 10 g/kg (guinea pig body weight) without administering sphingomyelin (group A), a group to which the sphingomyelin raw material of Example 1 was administered at a dose of 2 mg/kg (guinea pig body weight) in terms of the amount of sphingomyelin (group B), a group to which the sphingomyelin raw material of Example 1 was administered at a dose of 5 mg/kg (guinea pig body weight) in terms of the amount of sphingomyelin (group C), and a group to which the sphingomyelin raw material of Example 1 was administered at a dose of 10 mg/kg (guinea pig body weight) in terms of the amount of sphingomyelin (group D). The oral administration to each group was performed once daily using a sonde, and the guinea pigs were raised for 4 weeks. The sphingomyelin raw material of Example 1 was suspended in 10 g of a saline, and this suspension was orally administered to each of the groups B to D. Influence on pigmentation in the back skin of the guinea pigs in each group was measured with a colorimeter (CHROMA METER CR-200) manufactured by MINOLTA at the start of sample administration and at the completion of sample administration. A lightness recovery rate from the start of sample administration was calculated. The results are shown in Table 14.

TABLE 14

| Group | Sphingomyelin dose (mg/kg) | Lightness recovery rate (%) |
|---|---|---|
| A | 0 | 31 |
| B | 2 | 48 |
| C | 5 | 62 |
| D | 10 | 78 |

As shown in the results of Table 14, the lightness recovery rate after the 4-week oral administration was as low as 31% in the group A but was 48% in the group B, 62% in the group C, and 78% in the group D, up to 2.5 times larger than that in the group A.

This demonstrated that a lightness recovery rate is enhanced by the oral administration of sphingomyelin. Specifically, it was confirmed that orally administered sphingomyelin has an anti-pigmentation effect. In this context, it was demonstrated that such an effect was observed by the oral administration of sphingomyelin at a dose of 2 mg/kg (guinea pig body weight) or more and is significant in the oral administration at a dose of 5 mg/kg (guinea pig body weight) or more.

Test Example 17

Sphingomyelin was tested for its anti-inflammatory effect according to the method described in Japanese Patent Laid-Open No. 1-163125.

The anti-inflammatory effect of sphingomyelin was tested by a carrageenin-induced footpad edema method.

Specifically, a test subject shown in Table 15 was suspended in an aqueous solution containing 0.5% carboxymethylcellulose and orally administered (100 mg/kg) to male Wistar rats (body weight: 110 to 130 g, 8 individuals per group) according to the method of Winter et al. (Proceedings of the Society for Experimental Biology & Medicine, vol. 111, pp. 554, 1962). After 1 hour, 0.1 ml of a saline solution containing 1% λ-carrageenin serving as an inflammatory substance was hypodermically administered to either hind footpad of the rats to induce edema. The volume of the footpad of each rat was measured in a given period of time before and after inflammatory substance administration, and a rate of increase in footpad volume (V1) was determined. An aqueous solution containing 0.5% carboxymethylcellulose and no test substance was administered to rats in a control group. A rate of increase in footpad volume (V0) attributed to the injection of λ-carrageenin was measured in the control group in the same way as above. An carrageenin-induced edema inhibition rate (%) was calculated according to the calculation formula: (V0−V1)×100/V0 and used as the anti-inflammatory activity of the test substance. A higher value of this inhibition rate indicates higher anti-inflammatory activity. The inhibition rate values measured 5 hours after λ-carrageenin injection are shown in Table 15. As is evident from the results shown in Table 15, it was demonstrated that sphingomyelin exhibits a stronger edema inhibition rate than that of indomethacin or sialic acid and has a strong anti-inflammatory effect.

TABLE 15

| Test substance | Dose (mg/kg) | Inhibition rate (%) |
|---|---|---|
| Sphingomyelin (Example 1) | 100 | 40.2 |
| Indomethacin | 100 | 37.5 |
| Sialic acid (derived from milk) | 100 | 38.1 |

Test Example 18

Confirmation of Effect of Improving Learning Ability

The sphingomyelin raw material obtained in Example 1 was used to conduct a water maze experiment for the purpose of examining the influence of orally taken sphingomyelin on learned behavior. In this context, the experiment was conducted according to the method described in "Test Example 2" of Japanese Patent Laid-Open No. 9-301874. First, 8-week-old male SD rats (Charles River Laboratories, Japan) were preliminarily raised for 7 days using a standard diet (AIN-93G) and then divided into 3 groups each containing 6 individuals. Each group was allowed to take feed having composition shown in Table 16 for 10 days. In this context, the rats were raised under conditions involving room temperature of 24° C., humidity of 60%, and light-dark (12 hour/12 hour) control and were allowed to freely take deionized water.

TABLE 16

| | Composition of feed (%) | | |
|---|---|---|---|
| | Control group | Soybean lecithin group | Present invention group |
| α-corn starch | 13.2 | 13.2 | 13.2 |
| Corn starch | 39.7 | 39.7 | 39.7 |
| Milk casein | 20.0 | 20.0 | 20.0 |
| White soft sugar | 10.0 | 10.0 | 10.0 |
| Soybean oil | 7.0 | 5.0 | 5.0 |
| Crystalline cellulose powder | 5.0 | 5.0 | 5.0 |
| Mineral mixture [1] | 3.5 | 3.5 | 3.5 |
| Vitamin mixture [2] | 1.0 | 1.0 | 1.0 |
| L-cystine | 0.3 | 0.3 | 0.3 |
| Choline bitartrate | 0.25 | 0.25 | 0.25 |
| Tertiary butylhydroquinone | 0.0014 | 0.0014 | 0.0014 |
| Soybean lecithin [3] | | 2.0 | |
| Sphingomyelin raw material (Example 1) | | | 2.0 |

[1] AIN-93G/mineral mixture,
[2] AIN-93G/vitamin mixture,
[3] Basis LP20 (The Nisshin OilliO Group, Ltd.)

Subsequently, a "water filled multiple T-maze" was prepared by arranging combined T-mazes with 11 choice points in a water tank of 120 cm long, 120 cm wide, and 40 cm deep. A water maze experiment was conducted at a water temperature of 23 to 24° C. according to the method of Ishizaki (Ishizaki, Exp. Anim., vol. 27, pp. 9-12, 1978). First, the rats were separately acclimatized by 5 trials in a straight waterway a day before the test. Next, each rat was given 3 trials in the water maze for 4 consecutive days of the test. The length of time taken to swim from the start to the goal of the water maze was measured. The results are shown in Table 17.

TABLE 17

| | Length of time taken to swim to goal (second) | | | |
|---|---|---|---|---|
| | 1st day | 2nd day | 3rd day | 4th day |
| Control group | 55 ± 14 | 40 ± 12 | 29 ± 7 | 20 ± 5 |
| Soybean lecithin group | 50 ± 11 | 35 ± 9 | 25 ± 5 | 18 ± 4 |
| Present invention group | 33 ± 10 | 25 ± 6 | 18 ± 5 | 17 ± 6 |

On the 1st to 3rd days of the water maze experiment, the length of time taken to swim from the start to the goal was significantly shorter in the present invention group (group that took feed containing 2% of the sphingomyelin raw material obtained in Example 1) than in the control group or the soybean lecithin group (group that took feed containing 2% of Nisshin OilliO Basis LP20 having a soybean lecithin content of approximately 95%). This result demonstrated that sphingomyelin has an effect of improving learning ability.

Example 2

Raw materials were mixed according to formulation shown in Table 18 and then compressed into 1 g by a standard method to produce the pharmaceutical agent of the present invention in a tablet form.

TABLE 18

| Hydrous crystalline glucose | 83.5 (% by weight) |
|---|---|
| Sphingomyelin raw material (sphingomyelin content: 10%, Phospholipid 500, manufactured by Fonterra) | 10.0 |
| Mineral mixture | 5.0 |
| Sugar ester | 1.0 |
| Flavor | 0.5 |

In this context, this pharmaceutical agent (1 g) contained 10 mg of sphingomyelin.

Example 3

50 g of a sphingomyelin raw material having a sphingomyelin content of 25% (Phospholipid 700, manufactured by Fonterra) was dissolved as the agent of the present invention in 4950 g of deionized water, and the solution was heated to 50° C. and then mixed by stirring at 6000 rpm for 30 minutes using a TK homomixer (TK ROBO MICS; manufactured by Tokushu Kika Kogyo Co., Ltd.) to obtain a sphingomyelin solution having a sphingomyelin content of 250 mg/100 g. Into 4.0 kg of this sphingomyelin solution, 5.0 kg of casein, 5.0 kg of soybean proteins, 1.0 kg of fish oil, 3.0 kg of perilla oil, 18.0 kg of dextrin, 6.0 kg of a mineral mixture, 1.95 kg of a vitamin mixture, 2.0 kg of an emulsifier, 4.0 kg of a stabilizer, and 0.05 kg of a flavor were formulated, and this formulation was packaged into a 200-ml retort pouch and sterilized at 121° C. for 20 minutes using a retort sterilizer (primary pressure vessel, TYPE: RCS-4CRTGN, manufactured by Hisaka Works, Ltd.) to produce 50 kg of a liquid nutritional composition comprising the agent of the present invention. In this context, this liquid nutritional composition contained 20 mg of sphingomyelin per 100 g.

Example 4

10 g of a sphingomyelin raw material having a sphingomyelin content of 10% (Phospholipid 500, manufactured by Fonterra) was dissolved as the agent of the present invention in 700 g of deionized water, and the solution was heated to 50° C. and then mixed by stirring at 9500 rpm for 30 minutes using an ultra-disperser (ULTRA-TURRAX T-25; manufactured by IKA, Japan). To this solution, 40 g of sorbitol, 2 g of an acidulant, 2 g of a flavor, 5 g of pectin, 5 g of a whey protein concentrate, 1 g of calcium lactate, and 235 g of deionized water were added and mixed by stirring, and this mixture was then packaged into 200-ml cheerpacks and sterilized at 85° C. for 20 minutes. Then, the cheerpacks were stoppered to prepare 5 packs (interior content: 200 g) of food products in a gel form comprising the agent of the present invention. All the food products in a gel form thus obtained were confirmed to be free from precipitation or the like and have no abnormal taste. In this context, this food product in a gel form contained 100 mg of sphingomyelin per 100 g.

Example 5

2 g of an acidulant was dissolved in 700 g of deionized water. Then, in this solution, 10 g of a sphingomyelin raw material having a sphingomyelin content of 25% (Phospholipid 700, manufactured by Fonterra) was dissolved as the agent of the present invention, and the solution was heated to 50° C. and then mixed by stirring at 9500 rpm for 30 minutes using an ultra-disperser (ULTRA-TURRAX T-25; manufactured by IKA, Japan). To this solution, 100 g of maltitol, 20 g of reduced starch syrup, 2 g of a flavor, and 166 g of deionized water were added, and the mixture was then packaged into 100-ml glass bottles and sterilized at 90° C. for 15 minutes. Then, the bottles were stoppered to prepare 10 bottles (interior content: 100 ml) of drink products comprising the agent of the present invention. All the drink products thus obtained were confirmed to be free from precipitation and have no abnormal taste. In this context, this drink product contained 250 mg of sphingomyelin per 100 g.

Example 6

2 kg of a sphingomyelin raw material having a sphingomyelin content of 4% (SM-4, manufactured by Corman) was dissolved as the agent of the present invention in 98 kg of deionized water, and the solution was heated to 50° C. and then mixed by stirring at 3600 rpm for 40 minutes using a TK homomixer (MARK II 160 model, manufactured by Tokushu Kika Kogyo Co., Ltd.) to obtain a sphingomyelin solution having a sphingomyelin content of 80 mg/100 g. Into 10 kg of this sphingomyelin solution, 12 kg of soybean cake, 14 kg of skimmed milk powder, 4 kg of soybean oil, 2 kg of corn oil, 23.2 kg of palm oil, 14 kg of corn starch, 9 kg of flour, 2 kg of bran, 5 kg of a vitamin mixture, 2.8 kg of cellulose, and 2 kg of a mineral mixture were formulated, and this formulation was sterilized at 120° C. for 4 minutes to produce 100 kg of feed for dog raising comprising the agent of the present invention. In this context, this feed for dogs contained 8 mg of sphingomyelin per 100 g.

Industrial Applicability

A pharmaceutical agent of the present invention which contains sphingomyelin as an active ingredient and is any of preventive or therapeutic agents for various diseases, or a food and drink product or feed comprising any of these agents can be used in the prevention or treatment of the disease, improvement in symptoms, and so on, and is therefore very useful.

The invention claimed is:

1. A method for reducing hangover symptoms or shortening the recovery time from drunken symptoms comprising administering to a person in need of such treatment a pharmaceutical agent which contains sphingomyelin in an amount effective to reduce hangover symptoms or shorten the recovery time from drunken symptoms.

2. The method according to claim 1, wherein the sphingomyelin is derived from milk.

3. The method according to claim 1, wherein the step of administering a pharmaceutical agent comprises administering a food, drink product, or feed which contains sphingomyelin in an amount effective to reduce hangover symptoms or shorten the recovery time from drunken symptoms.

4. The method according to claim 2, wherein the step of administering a pharmaceutical agent comprises administering a food, drink product, or feed which contains sphingomyelin in an amount effective to reduce hangover symptoms or shorten the recovery time from drunken symptoms.

* * * * *